United States Patent [19]

Beach

[11] Patent Number: 5,294,538
[45] Date of Patent: Mar. 15, 1994

[54] METHOD OF SCREENING FOR ANTIMITOTIC COMPOUNDS USING THE CDC25 TYROSINE PHOSPHATASE

[75] Inventor: David H. Beach, Huntington Bay, N.Y.

[73] Assignee: Cold Spring Harbor Labs., Cold Spring Harbor, N.Y.

[21] Appl. No.: 878,640

[22] Filed: May 5, 1992

Related U.S. Application Data

[63] Continuation-in-part of Ser. No. 793,601, Nov. 18, 1991.

[51] Int. Cl.$^5$ .................. C12Q 1/42; C12P 21/06; C07H 19/00; C07H 21/00
[52] U.S. Cl. ..................... 435/21; 435/69.1; 435/69.3; 435/69.7; 435/172.3; 435/193; 435/194; 435/320.1; 514/44; 536/22.1; 536/23.1; 536/23.2; 536/23.5
[58] Field of Search .................. 435/69.7, 21, 69.1, 435/69.3, 172.3, 193, 194, 320.1; 514/44; 536/22.1, 23.1, 23.2, 23.5

[56] References Cited

PUBLICATIONS

Glover "Expression of cloned DNA in E. coli plasmid"-'in *Gene Cloning* 1984, pp. 110–129.
Gautier, J. et al., Cell, 67:197–211 (Oct. 4, 1991).
Dunphy, W. G. and A. Kumagai, Cell, 67:189–196 (Oct. 4, 1991).
Nagata, A. et al., *The New Biologist*, 3:959–968 (Oct., 1991).

*Primary Examiner*—Robert A. Wax
*Assistant Examiner*—Hyosuk Kim
*Attorney, Agent, or Firm*—Bertram I. Rowland

[57] ABSTRACT

A method of identifying compounds or molecules which alter (enhance or inhibit) stimulation of kinase activity of pre-MPF and, thus, alter (enhance or inhibit) activation of MPF and entry into mitosis. The present method thus makes it possible to identify compounds or molecules which can be administered to regulate the cell cycle; such compounds are also the subject of this invention.

4 Claims, 5 Drawing Sheets

METHOD OF SCREENING FOR ANTIMITOTIC COMPOUNDS USING THE CDC25 TYROSINE PHOSPHATASE

FUNDING

Work described herein was funded by the National Institutes of Health (GM 69620) and the Howard Hughes Medical Institute. The United States Government has certain rights in the invention.

RELATED APPLICATION

This application is a continuation-in-part of U.S. Ser. No. 07/793,601, entitled Novel Human cdc25 Genes, Encoded Products and Uses Thereof, by David H. Beach, filed Nov. 18, 1991.

BACKGROUND

A universal intracellular factor, the "M phase-promoting factor" (MPF), triggers the G2/M transition of the cell cycle in all organisms. In late G2, it is present as an inactive complex of tyrosine-phosphorylated p34$^{cdc2}$ and unphosphorylated cyclin B$^{cdc13}$. In M phase, its activation as an active MPF displaying histone H1 kinase activity originates from the specific tyrosine dephosphorylation of the p34$^{cdc2}$ subunit by the tyrosine phosphatase p80$^{cdc25}$. Little is known about the signals which control or determine timing of MPF activation and entry into mitosis or about ways in which those signals can be blocked or enhanced, resulting in inhibition or facilitation of entry into mitosis. A means of identifying agents which do so would be useful, particularly because it would provide a way of controlling mitosis

SUMMARY OF THE INVENTION

The present invention is a method of identifying compounds or molecules which alter (enhance or inhibit) stimulation of kinase activity of pre-MPF and, thus, alter (enhance or inhibit) activation of MPF and entry into mitosis The present method thus makes it possible to identify compounds or molecules which can be administered to regulate the cell cycle; such compounds are also the subject of this invention.

In the subject method, a compound or molecule is assessed for its effect on an essential cell cycle-regulating component, cdc25 (e.g., cdc25A, cdc25B, cdc25C). As described in co-pending application U.S. Ser. No. 07/793,601, cdc25 has been shown to be the tyrosine phosphatase which dephosphorylates cdc2, leading to MPG activation and transition from late G2 to M phase and mitosis. The present method makes use of a cell cycle-specific target and, thus, provides a highly specific mechanism-based screen for agents (compounds or molecules) which alter mitosis, particularly antimitotic agents.

In the subject method, a molecule or compound to be assessed for its ability to inhibit cdc25 tyrosine phosphatase activity is combined with cdc25 and a substrate of cdc25 tyrosine phosphatase activity. The resulting combination is maintained under conditions appropriate for cdc25 to act upon the substrate. It is then determined whether cdc25 acted upon the substrate when the compound being assessed was present; decreased activity (lack of activity or less activity than is evident when the compound is not present) indicates the compound is an inhibitor. The extent to which cdc25 acts upon the substrate in the presence of the compound is compared with the extent to which cdc25 acts on the substrate in the absence of the compound (in comparison with a control). If cdc25 activity is less in the presence of the compound, the compound is an inhibitor of cdc25.

In the subject method, a potential antimitotic agent (i.e., an agent to be assessed for an anti-mitotic effect) is combined with cdc25, which is either cdc25 protein or a fusion protein (e.g., recombinant p80$^{cdc25}$ present in a two-component fusion protein in which cdc25 is joined with a second component, such as glutathione-S-transferase). Subsequently, the effect of the potential antimitotic agent on the phosphatase activity of cdc25 is determined. p80$^{cdc25}$ protein has been shown, as described herein, to have p-nitrophenylphosphate phosphatase activity. Thus, the inhibitory effect of the agent being tested on cdc25 can be assessed using p-nitrophenylphosphate or inactive cyclin/cdc2 as substrate. Results obtained (e.g., the extent of inhibition of cdc25 phosphatase activity) are particularly valuable, since they demonstrate the effect of the agent tested on a target which is particularly well suited for detecting antimitotic agents because of its direct role in controlling entry of cells into M phase.

DETAILED DESCRIPTION OF THE INVENTION

Figure 1:
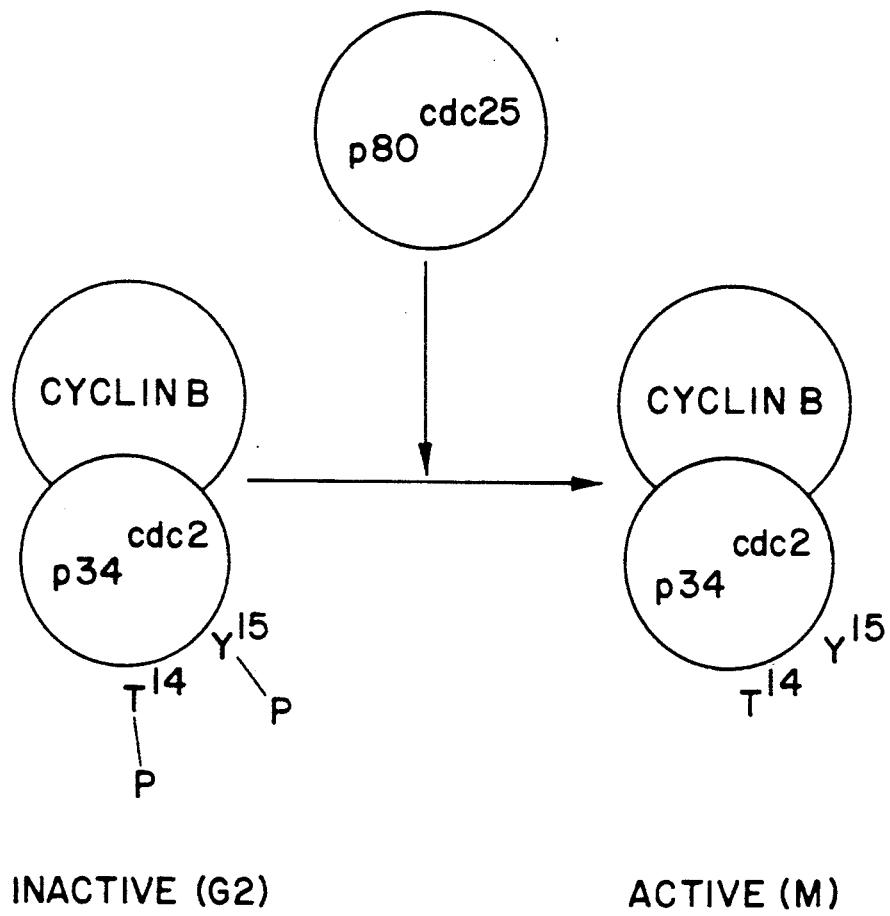
FIG. 1 is a schematic representation of the control by p80$^{cdc25}$ of activtion of inactive pre-MPF(G2) to active MPF (M phase).

Described herein is an assay in which cdc25 tyrosine phosphatase, such as cdc25 protein or recombinant human cdc25 tyrosine phosphatase, is used as a cell cycle-specific target to screen for compounds which alter entry into mitosis (passage from late G2 into the M phase). Results of the assay (i.e., the ability of the compound being tested to inhibit cdc25) are determined by known techniques (e.g., colorimetrically, by immunoassay techniques or by detecting enzymatic activity (e.g., histone kinase activity)). In one embodiment of the subject method, a colorimetric assay has been used, as described, to determine the ability of compounds to inhibit the cdc25 tyrosine phosphatase, which is an activator of the protein kinase MPF. As described herein, a glutathione-S-transferase/cdc25A tyrosine phosphatase fusion protein produced in *Escherichia coli* and purified displays a phosphatase activity towards p-nitrophenylphosphate. This fusion protein, designated GST-cdc25A, has been used to assess the inhibitory effect of compounds on cdc25 phosphatase activity. In a similar manner, as also described herein, other fusion proteins can be produced and used in the same or a similar assay format. These fusion proteins can differ from GST-cdc25A in either or both of their components. For example, a component other than GST (e.g., maltase binding protein) can be included in the fusion protein with cdc25A. Alternatively, another member of the cdc25 family (e.g., cdc25B, cdc25C) can be the tyrosine phosphatase component. In another embodiment, cdc25 protein is used.

The present method is a simple and rapid screening test which, in one embodiment, uses a fusion protein such as recombinant p80$^{cdc25}$, assayed through its p-nitrophenylphosphate phosphatase activity, as a target to test for potential antimitotic compounds. The method has been carried out as a rapid colorimetric microtitration plate assay to test compounds currently used in cancer therapy, and a compound recognized to be a tyrosine phosphatase inhibitor. The therapeutic compounds tested did not display an ability to inhibit cdc25, in the assay as described; the reported tyrosine phosphatase inhibiter (vanadate) was shown, however, to totally inhibit cdc25. Thus, the present method has been shown to be useful in identifying compounds which inhibit an essential cell cycle-regulating component; it provides a highly specific screen for antimitotic drugs.

In one embodiment of the present method, a fusion protein which includes cdc25 is combined, under appropriate conditions, with: 1) an agent to be assessed for its effects on cdc25 and, thus, on passage from late G2 into the M phase; and 2) an appropriate cdc25 substrate, such as p-nitrophenylphosphate or inactive cdc2/cyclin B. The resulting combination is maintained for sufficient time for cdc25 to act upon the cdc25 substrate and the reaction is terminated (e.g., by gross alteration of the pH of the combination). Phosphatase activity of the combination is determined using a known technique, such as by measuring the optical density of the combination and comparing it with a predetermined standard or a control (e.g., a predetermined relationship between optical density and extent of cdc25 inhibition or a combination which includes the same components as the "test" combination except for the agent being assessed).

The fusion protein used in the present method can be produced by known genetic engineering techniques, as described in Example 1. That is, a DNA or RNA construct encoding the fusion protein is introduced into an appropriate host cell, in which the construct is expressed, thus producing the fusion protein. The fusion protein is separated (and, preferably, purified) from the host cell and used in the assay. Alternatively, the fusion protein can be produced by joining the two separately produced components. As described in Example 2, a fusion protein in which the two components are glutathione-S-transferase and human cdc25A has been produced and used in the subject method.

In a second embodiment, cdc25 protein, such as cdc25A, cdc25B or cdc25C protein, can be used in the subject method. In this embodiment, cyclin/cdc2 can be used as the cdc25 substrate; an agent to be tested is combined with cdc25 protein and cyclin/cdc2 and the tyrosine phosphatase activity of cdc25 is assessed, as described above. Results are compared with a predetermined standard or with a control. (See Example 1).

The cdc25 substrate used can be any synthetic or naturally-occurring substance toward which cdc25 demonstrates phosphatase activity. In the embodiment described herein, the cdc25A substrate used is p-nitrophenylphosphate. Other substrates which can be used include peptides that mimic the site of cdc2 phosphorylation or the full inactive cdc2/cyclinB pre-enzyme complex. Others can be identified by using known methods of determining phosphatase activity.

Agents to be tested for their ability to alter cdc25 tyrosine phosphatase activity can be those produced by bacteria, yeast or other organism or those produced chemically. The compounds tested as described herein included 15 drugs currently used in cancer therapy (see the Table) and vanadate, a recognized tyrosine phosphatase inhibitor. The 15 therapeutic agents showed no inhibitory activity. In contrast, vanadate was shown to totally inhibit GST-cdc25A phosphatase. The present method is useful to identify agents potentially effective as antiproliferative agents and agents which are useful in treating or preventing inflammation or psoriasis, etc.

Alternatively, the present method can be used to identify compounds which enhance cdc25 tyrosine phosphatase activity.

The present invention will now be illustrated by the following examples, which are not intended to be limiting in any way.

Materials and Methods

Chemicals sodium fluoride, sodium orthovanadate, nitrophenol, cis-platinum, isopropyl $\beta$-D-thiogalactopyranoside (IPTG), 1-methyladenine, dithiothreitol (DDT), EGTA, EDTA, MOPS, $\beta$-glycerophosphate, leupeptin, aprotinin, soybean trypsin inhibitor, benzamidine, histone H1 (type III-S), CNBr-activated sepharose 4B, glutathione-agarose (G 4510), glutathione (G 4251), nonidet P40 (NP40), Tris, LB Broth base, were obtained from Boehringer-Mannheim, p-nitrophenylphosphate (p-NPP) (disodium salt hexahydrate, ref. 12.886.82) was from Janssen Chimica.

$[\gamma-^{32}P]$-ATP (PB 168) and $^{125}I$]-protein A (IM 144) were obtained from Amersham.

G1 anti-p34$^{cdc2}$ antibodies and anti-p80$^{cdc25}$ antibodies (directed against the cdc25C phosphatase peptide H$_2$N-QEGERQLREQIALLVKDMS-COOH) were kindly provided by Dr. G. Draetta (Heidelberg), anti-cyclin B$^{cdc13}$ (starfish) antibodies were generously donated by Dr. T. Kishimoto (Tokyo), anti-phosphotyrosine antibodies were generously given by Dr. J. Y. J. Wang (La Jolla), antibodies against H$_2$N-VEKIGEGTYGV-VYKARHKLS-COOH (a p34$^{cdc2}$ peptide containing the regulatory threonine-14 and tyrosine-15 residues) were kindly provided by Dr. L. Tung (Philadelphia). This last antibody does not recognize tyrosine-phosphorylated p34$^{cdc2}$ but only tyrosinedephosphorylated p34$^{cdc2}$.

Buffers

Oocyte homogenization buffer contained 60 mM $\beta$-glycerophosphate, 15 mM p-NPP, 20 mM MOPS pH 7.2, 15 mM EGTA, 15 mM MgCl$_2$, 1 mM DTT, 0.1 mM sodium vanadate, 0.1 mM sodium fluoride, 10 $\mu$g leupeptin/ml, 10 $\mu$g aprotinin/ml, 10 $\mu$g soybean trypsin inhibitor/ml, 100 $\mu$M benzamidine. This buffer had previously been shown to stabilize the starfish meiotic oocyte M phase-specific histone H1 kinase (Pelech, S. L. et al., *Biochemistry* 26:7960–7968 (1987)).

Bead buffer contained 50 mM Tris pH 7.4, 5 mM NaF, 250 mM NaCl, 5 mM EDTA, 5 mM EGTA, 0.1% NP40, 10 $\mu$g leupeptin/ml, 10 $\mu$g aprotinin/ml, 10 $\mu$g soybean trypsin inhibitor/ml and 100 $\mu$M benzamidine.

Tris-Buffered Saline (TBS) contained 50 mM Tris pH 7.4, 150 mM NaCl.

Phosphate-Buffered Saline (PBS) contained 9.6 mM phosphate, 2.7 mM KCl, 140 mM NaCl.

Lysis buffer contained 1% NP40, 1 mM EDTA, 1 mM DTT, 10 μg leupeptin/ml, 10 μg aprotinin/ml, 10 μg soybean trypsin inhibitor/ml and 100 μM benzamidine/ml in PBS.

Tris buffer A contained 50 mM Tris pH 8.0, 50 mM NaCl, 1 mM EDTA, 1 mM DTT.

Elution buffer contained 10 mM glutathione in Tris buffer A.

Preparation of G2 and M Phase Oocytes

G2 and M phase oocytes were prepared as follows: Gonads were removed from mature starfish (*Marthasterias glacialis*), collected in Northern Brittany. They were either directly frozen in liquid nitrogen and kept at −80° C. (G2 oocytes) or incubated with 10 μM 1-methyladenine in natural seawater for 10 min (M. oocytes). By that time all the oocytes had entered the M phase, although they were still in the gonads. These were then removed from the incubation medium, rapidly blotted on filter paper, directly frozen in liquid nitrogen and kept at −80° C.

Transfer buffer contained 39 mM glycine, 48 mM Tris, 0.37% SDS, 20% methanol.

Bacterial Growth and cdc25A Induction

An *E. coli* strain (BL 21(DE3)) containing a plasmid encoding the genes fusion construct of glutathione-S-transferase (GST) and human cdc25A under the control of IPTG was used (Galaktionov, K. and D. Beach, *Cell* 67:1181–1194 (1991)). *E. Coli* were first grown overnight at 37° C. in the presence of 100 μg ampicillin/ml LB medium. Four ml of this preculture were inoculated/liter of LB containing 100 μg ampicillin/ml. Incubation was pursued at 30° C. until the culture O. D. at 500 nm had reached a value between 0.8 and 1.00 (about 4–5 hrs). At this moment, 0.4 mM IPTG was added and the culture incubated at 25° C. for at least 7 hrs. Cells were then harvested by a 3000 g centrifugation for 15 min at 4° C. Pellets were kept frozen at −80° C. until extraction.

EXAMPLE 1: p80$^{cdc25}$ Controls p34$^{cdc2}$/cyclin B Activation

Inactive pre-MPF (G2) is constituted of cyclin B and p34$^{cdc2}$ phosphorylated on its threonine-14 and tyrosine-15 residues. p80$^{cdc25}$ is the phosphatase which dephosphorylates the tyrosine-15 residue, and possible threonine-14. Its action leads to activation of the p34$^{cdc2}$/cyclin B$^{cdc13}$ kinase responsible for induction of the G2/M transition. The interaction of these components and activation of inactive pre-MPF (G2) is represented in FIG. 1. An agent to be tested for its ability to alter stimulation of kinase activity is combined with the inactive pre-MPF (G2) and the effects, if any, are determined. If an agent tested is an inhibitor, the inactive pre-MPF will not be activated.

EXAMPLE 2: Production and Purification of GST-cdc25A Phosphatase

A fusion construct between the glutathione-S-transferase (GST) gene and human cdc25A was built in a plasmid vector (Galaktionov, K. and D. Beach, *Cell* 67:1181–1194 (1991)). Transfected and expressed in *E. coli*, it produces large amounts of the corresponding fusion protein which can be purified by affinity chromatography on glutathione-agarose beads. The protocols of production, purification and assay of the GST-cdc25A phosphatase is described in detail below. Production involves culture of recombinant *E. coli* and classical induction of GST-cdc25A expression by IPTG. One-step affinity-chromatography on glutathione-agarose allows the purification of the GST-cdc25A phosphatase. The optimum ratio of bacterial extract volume/glutathioneagarose volume was found to be 6–10 to 1. Glutathione-agarose can be easily recycled. GST-cdc25A was either preserved as the bacterial pellet (very stable), the supernatant of the centrifuged bacterial extract or after affinity-purification and in the presence of 40% glycerol (final volume).

The bacterial pellet was disrupted by sonication in lysis buffer at 4° C. The homogenate was centrifuged for 30 min at 4° C. at 100,000 g; the supernatant was recentrifuged under similar conditions; the final supernatant was then immediately mixed and rotated with glutathione-agarose beads (equilibrated with lysis buffer) for 30 min at 4° C. (6–10 volumes of supernatant/1 volume of packed beads). The glutathione-agarose beads were washed three times with 10 volumes of lysis buffer, followed by four washes with 10 volumes of Tris buffer A. Elution of the fusion protein was induced by 3–4 successive washes with 10 mM glutathione in Tris buffer A. The efficiency of the elution was monitored by a phosphatase assay. Active fractions were pooled and used directly or supplemented with 40% glycerol prior to storage 15 80° C.

Glutathione-agarose beads can be recycled by a wash with 1M NaCl, followed by equilibration with lysis buffer.

Figure 3B:
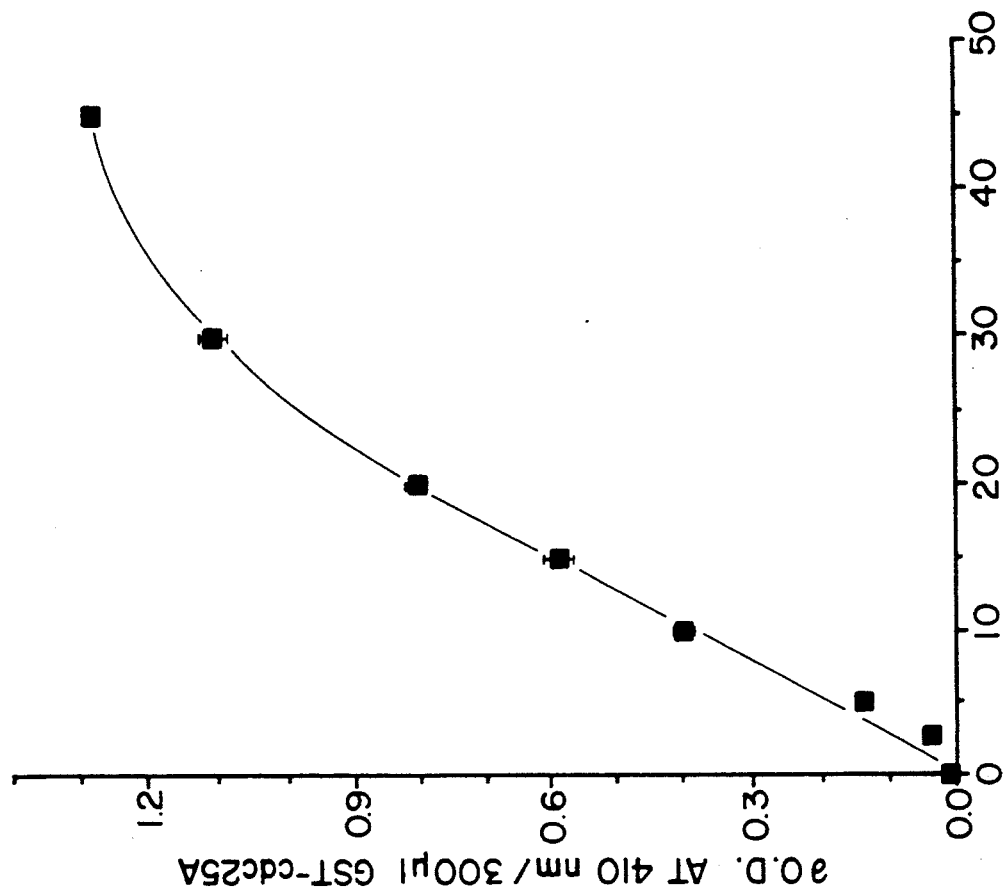
FIG. 3 is a graphic representation of GST-cdc25-pNPP phosphatase activity as a function of GST-cdc25A concentration (FIG. 3A) and as a function of duration of assay (FIG. 3B).
Figure 3A:
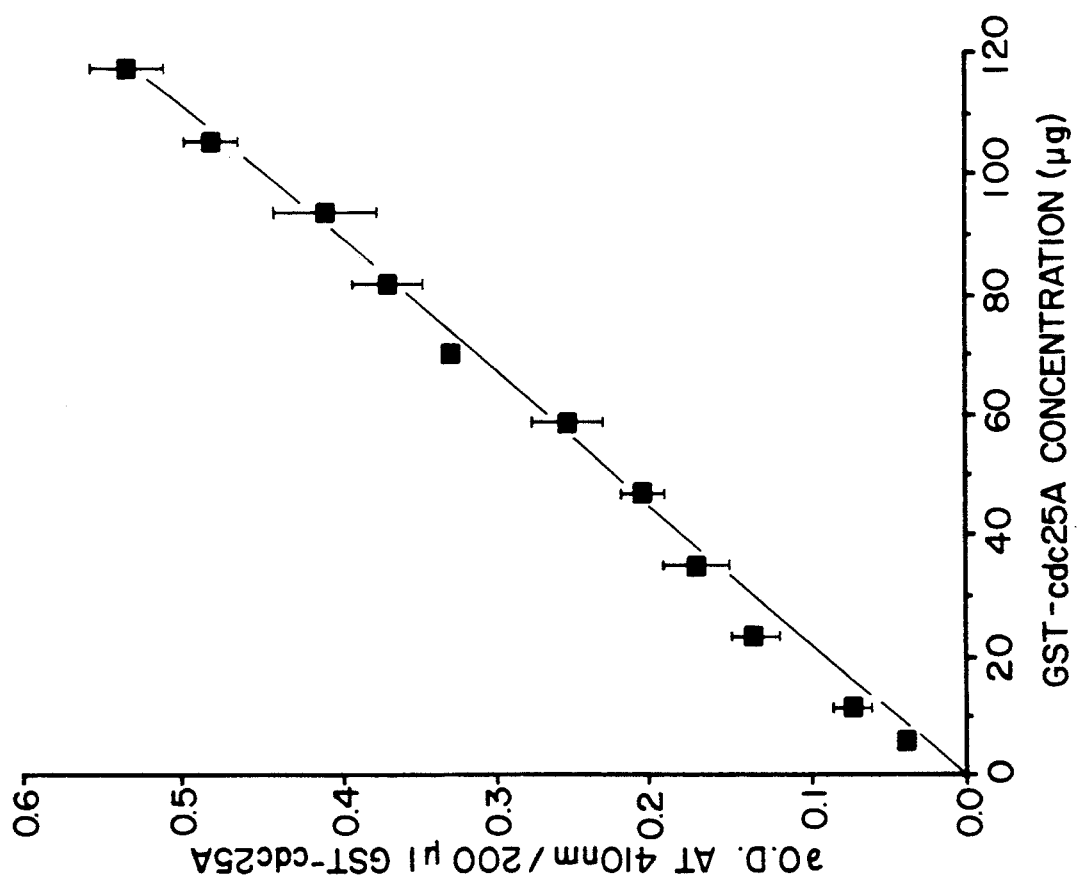
Figure 4B:
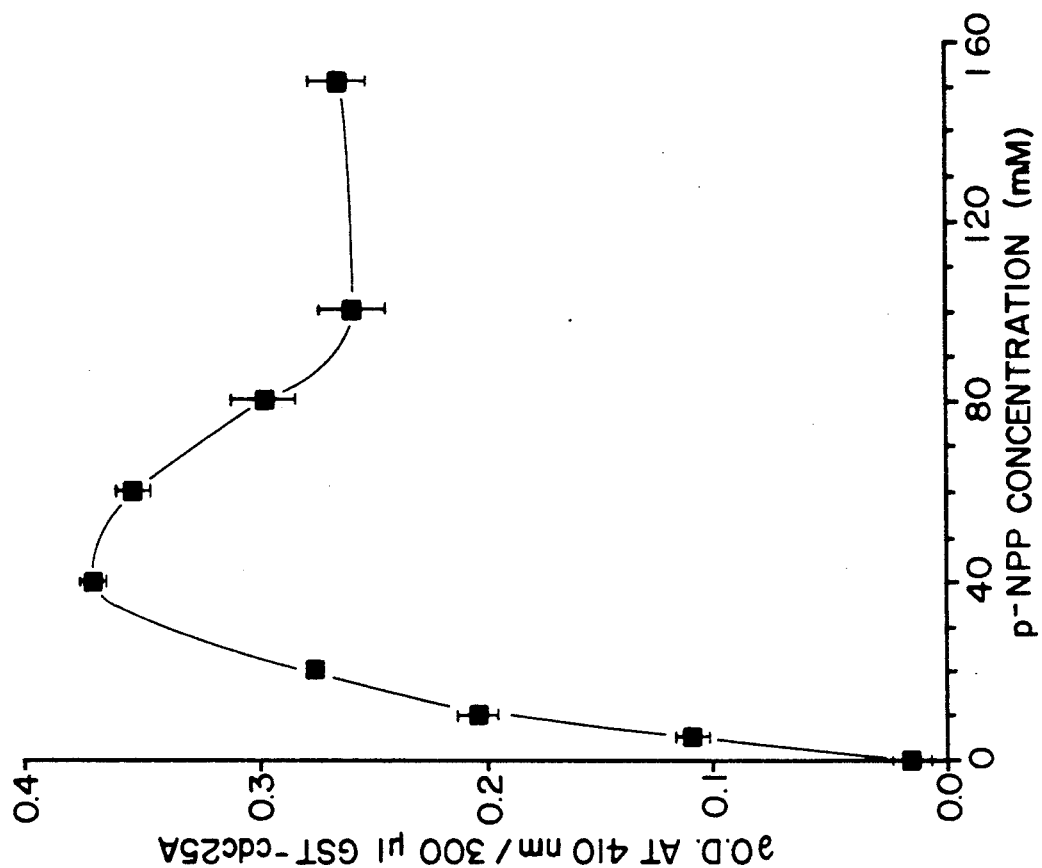
FIG. 4 is a graphic representation of GST-cdc25a activity as a function of DTT concentration (FIG. 4A) and p-NPP concentration (FIG. 4B).
Figure 4A:
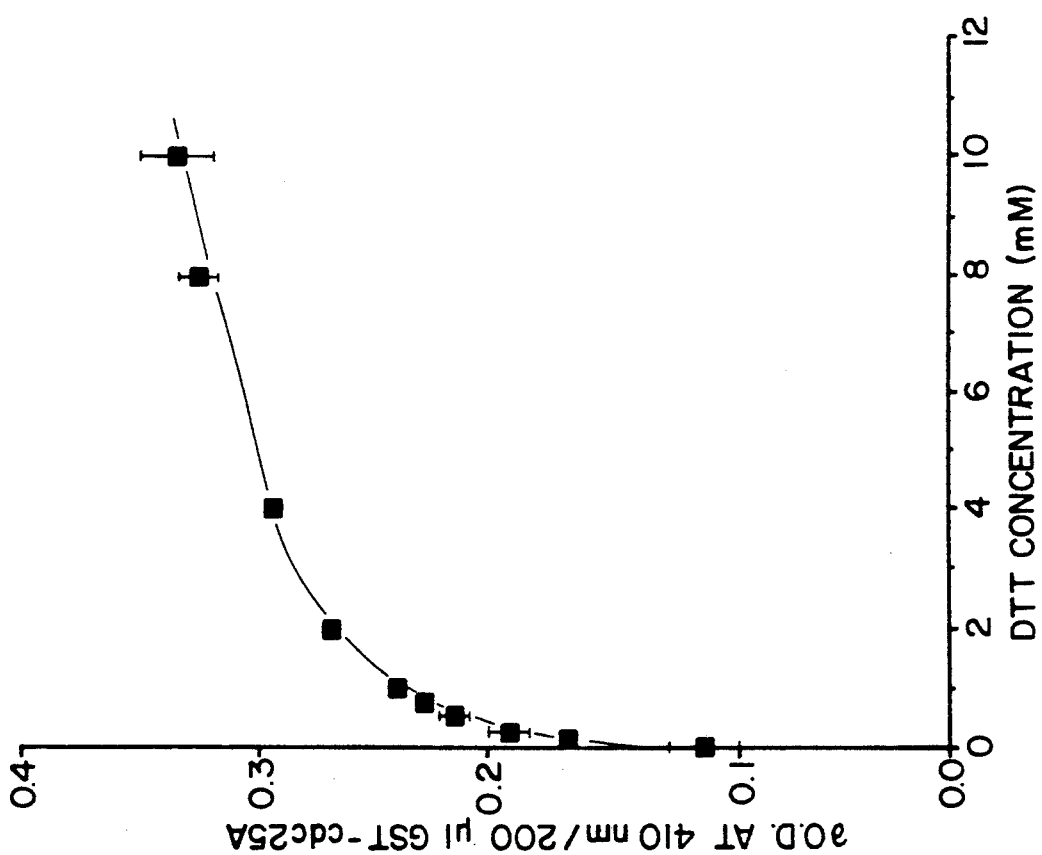

EXAMPLE 3: Assay of the GST-cdc25A Phosphatase Activity Towards p-Nitrophenylphosphate GST-cdc25A phosphatase activity can be very conveniently assayed using the chromogenic substrate p-nitrophenylphosphate (p-NPP). Optimal conditions for several parameters were determined with a one ml assay, as described below. Results are represented graphically in the figures: amount of GST-cdc25A phosphatase (FIG. 3A), duration of assay (FIG. 3B), DTT concentration (FIG. 4A), p-NPP concentration (FIG. 4B).

One ml assay: 100 μl of GST-cdc25A protein (diluted to an activity of a OD 410 nm=0.3/10 min) were mixed with 100 μl mM DTT (in Tris buffer A) and 700 μl of Tris buffer A. The assay was initiated by addition of 100 μl 500 mM p-NPP (in Tris buffer A). After 10 min incubation at 37° C., the assay was terminated by addition of 40 μl 5N NaOH and transfer of the tubes to 4° C. Absorbance at 410 nm was then measured and blank values (no GST-cdc25A protein but 10 min incubation) were subtracted.

This assay was then scaled down to 200 μl and conducted semi-automatically in 96-wells microtitration plates, as described in detail below. Each well is filled with 20 μl GST-cdc25A phosphatase, 140 μl Tris buffer A, 20 μl 100 mM DTT (in Tris buffer A); after 15 min equilibration at 37° C., reaction is initiated by addition of 20 μl 500 mM p-NPP (in Tris buffer A). After 60 min incubation absorbance at 405 nm is monitored in a microplate reader; blank values (no GST-cdc25A added) is subtracted Microtitration plate assay: 20 μl of GST-cdc25A protein (diluted to an activity of a O. D.405 nm=0.2–0.3/60 min) were mixed with 20 μl 100 mM DTT (in Tris buffer A) and 140 μl of Tris buffer A, in 96-wells microtitration plates (Corning). The plates were preincubated at 37° C. for 15 min in a Denley Wellwarm 1 microplate incubator. The assays were initiated by addition of 20 μl of 500 mM p-NPP (in Tris buffer A). After 60 min incubation at 37° C. absorbance at 405 nm was measured in a bioRad microplate reader. Blank values (no CST-cdc25A protein added) were automatically substracted.

Figure 2B:
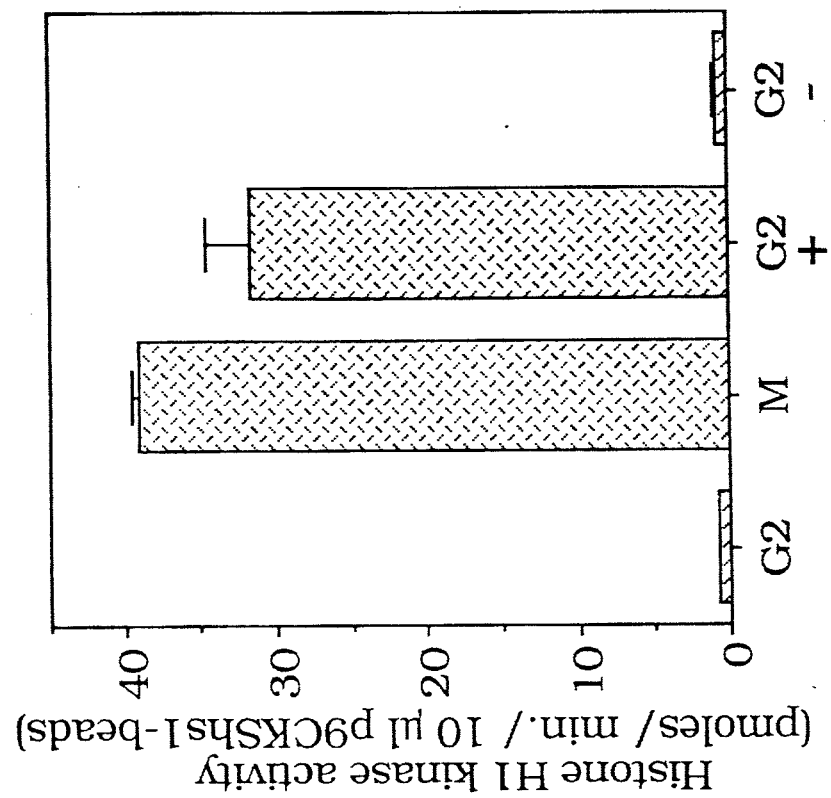
FIG. 2 is evidence that the GST-cdc25a fusion protein dephosphorylates p34$^{cdc2}$ (FIG. 2A) and activates the M phase-specific H1 kinase (MPF) FIG. 2B.
Figure 2A:
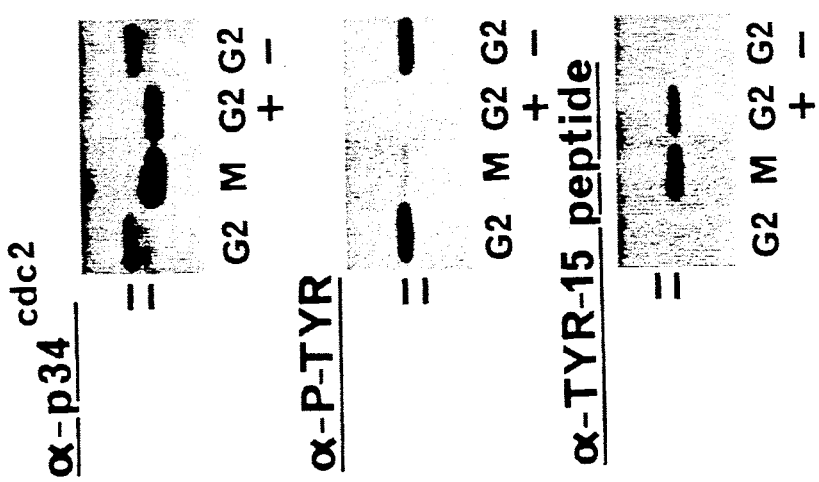

EXAMPLE 4: Tyrosine Dephosphorylation and Activation of the p34$^{cdc2}$/cyclin B$^{cdc13}$ Kinase by the Fusion Protein GST-cdc25A The ability of the GST-cdc25A fusion protein to dephosphorylate and activate the p34$^{cdc2}$/cyclin B$^{cdc13}$ kinase was demonstrated. p34$^{cdc2}$/cyclin B$^{cdc13}$ complex from G2-arrested starfish oocytes was immobilized on p9$^{CKShs1}$ agarose: it is constituted of tyrosine-phosphorylated p34$^{cdc2}$ and cyclin B$^{cdc13}$ (Arion, L. et al., Eur. J. Biochem.: (1992); Pondaven, P. et al., Genes and Development 4:9-17 (1990)). Treatment with purified GST-cdc25A protein induced almost complete tyrosine dephosphorylation of p34$^{cdc2}$ as shown (FIG. 2, left) by the p34$^{cdc2}$ mobility shift (upper panel), the loss of cross-reactivity with anti-phosphotyrosine antibodies (middle panel) and the appearance of cross-reactivity with an antibody directed against a p34$^{cdc2}$ peptide comprising the tyrosine-15 residue (lower panel). In addition, this tyrosine dephosphorylation lead to histone H1 kinase activation to a level close to that found in M phase oocytes (FIG. 2, right). By these criteria, the GST-cdc25A fusion protein appears to display all the physiological enzymatic activity of cellular p80$^{cdc25}$.

Assay of p34$^{cdc2}$/Cyclin B$^{cdc13}$ Kinase Activity

Oocyte extracts were prepared by homogenization of 1 g of G2 or M phase gonads per 2 ml homogenization buffer. After centrifugation for 10 min at 14,000 g at 4° C., the supernatants were loaded on p9$^{CKShs1}$-sepharose beads prepared as described in (Azzi, L. et al., Eur. J. Biochem.:in press (1992)) (400 μl supernatant/10 μl p9$^{CKShs1}$-beads). The tubes were kept under constant rotation at 4° C. for 30 min. After a brief centrifugation at 10,000 g and removal of the supernatant, the beads were washed three times with bead buffer and eventually exposed to purified GST-cdc25A phosphatase prior to H1 kinase assay or to immunoblotting analysis.

Histone H1 kinase assays were performed by incubation of 10 μl of packed p9$^{CKShs1}$-beads (loaded with G2 or M phase extrCTS) for 10 min at 30° C. with 15 μM [γ-32P] ATP (3,000 Ci/mmol; 1 mCi/ml) in the presence of 1 mg histone III/ml in a final volume of 40 μl. Assays were terminated by transferring the tube onto ice. After a brief centrifugation at 10,000 g, 30 μl aliquots of supernatant were spotted onto 2.5×3 cm pieces of Whatman P81 phosphocellulose paper, and after 20 sec, the filters were washed five times (for at least 5 min each time) in a solution of 10 ml phosphoric acid/liter of water. The wet filters were transferred into 6 ml plastic scintillation vials, 5 ml ACS (Amersham) scintillation fluid was added and the radioactivity of the samples measured in a Packard counter.

Electrophoresis and Western Blotting

Proteins bound to p9CKShs1-sepharose beads were recovered with 50 μl 2X Laemmli sample buffer. Samples were run in 10% SDS/polyacrylamide gels. Proteins were stained with Coomassie Blue or transferred to 0.1 μm nitrocellulose sheets (Schleicher & Schull) in a Milliblot/SDE system (Millipore) for 30 min at 2.5 mA/cm$^2$ in transfer buffer. The filters were subsequently blocked with TBS containing 3% bovine serum albumin for 1 hr at room temperature. The filters were then incubated overnight at 4° C. with g1 anti-p34CDC2 antibodies (1:1000 dilution), anti-p34$^{cdc2}$ peptide antibodies (1:500 dilution) or anti-phosphotyrosine antibodies (1 μg/ml). After four washes of 15 min each with TBS containing 0.2% NP40, the filters were treated with 1 μCi $^{125}$I-protein A (30 mCi/mg) in 3% bovine serum albumin in TBS for 2 hr at room temperature. After four 15 min washes with 0.2% NP40 in TBS, the filters were exposed overnight to hyperfilm MP (Amersham).

EXAMPLE 5: Detection of Inhibitors of Purified GST-cdc25A Phosphatase

Figure 5:
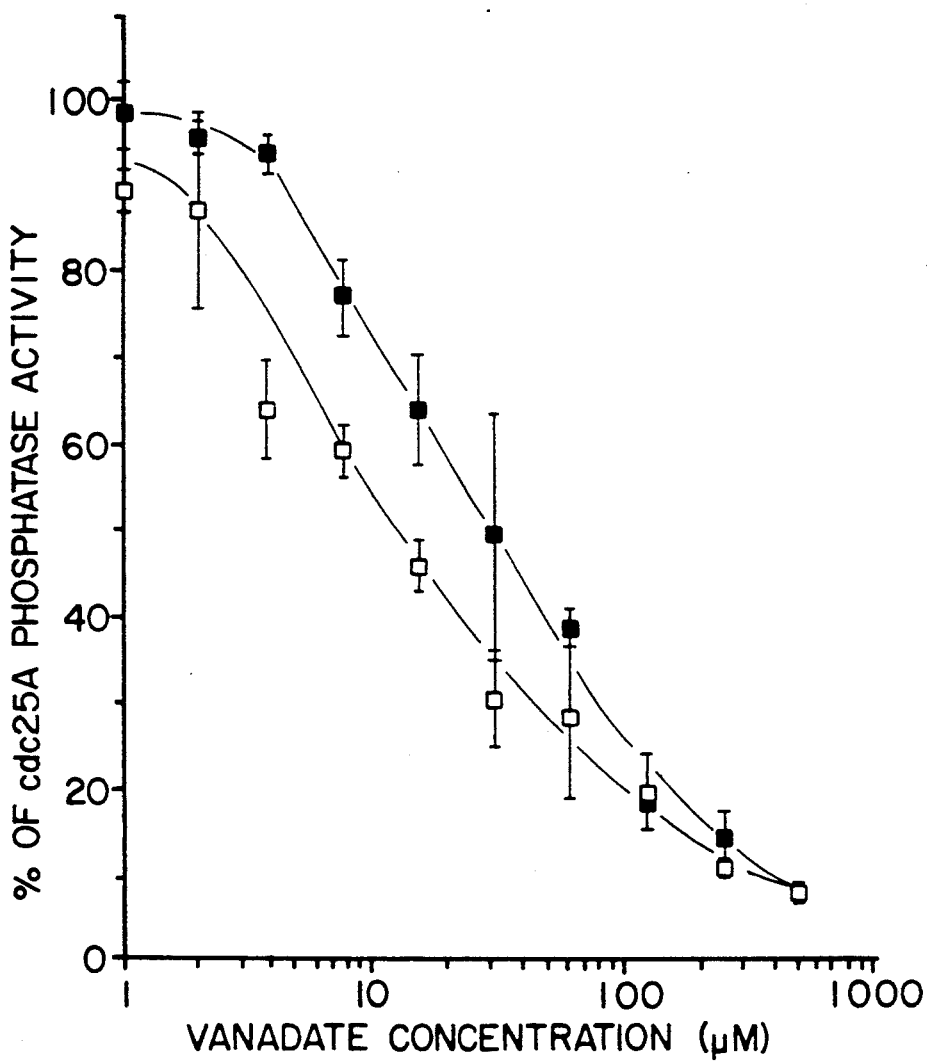
FIG. 5 is a graphic representation of the inhibitory effect of sodium orthovanadate on GST-cdc25A tyrosine phosphatase, in which phosphatase activity is expressed as % of activity in the absence of vanadate (mean±SD).

In a first series of experiments various antimitotic compounds currently used in cancer therapy were tested as potential inhibitors of the phosphatase (the Table). Most of them are reported to act as DNA damaging agents, as DNA intercalators, as topoisomerase 2 inhibitors or as compounds interfering with spindle microtubles. None of them displayed GST-cdc25A phosphatase inhibitory activity. As a positive control we then tested vanadate, a reported inhibitor of tyrosine phosphatases (Gordon, J. A., Methods in Enzymology pp.477-482 (1991)). This compound totally inhibites the GST-cdc25A phosphatase at concentrations above 500 μM (FIG. 5; $I_{50}=20$ μM).

TABLE

ANTIMITOTIC COMPOUNDS TESTED AS POTENTIAL INHIBITORS of p80$^{cdc25A}$

| Compounds | Range of Concentration Tested |
|---|---|
| Actinomycin D | 0.1–100 μg/ml |
| BCNU | 0.1–100 μg/ml |
| Carboplatin | 0 1–100 μg/ml |
| Chlormethine | 0.1–100 μg/ml |
| Cis-platinum | 0.1–100 μg/ml |
| Cyclophosphamide | 0.1–100 μg/ml |
| Dacarbazine | 0.1–100 μg/ml |
| Doxorubicin | 0.1–100 μg/ml |
| Etoposide | 0.1–100 μg/ml |
| Fluoro-uracil | 0.1–100 μg/ml |
| Girolline | 0.36–360 μg/ml |
| Methotrexate | 0.1–100 μg/ml |
| Novobiocin | 0.1–100 μg/ml |
| Vinblastine | 0.1–100 μg/ml |
| Vincristine | 0.1–100 μg/ml |

None of the compounds exhibited more than 5–10% inhibitory activity on the enzyme over the indicated range of concentration.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of identifying a compound which is an inhibitor of human CDC25 tyrosine phosphatase activity, comprising the steps of:
   a) combining:
      1) a compound to be assessed;
      2) CDC25 from a human source; and
      3) p-nitrophenyl phosphate;
   b) maintaining the combination produced in (a) under conditions appropriate for CDC25 to act upon p-nitrophenyl phosphate; and c) determining the extent of action of said CDC25 upon p-nitrophenyl phosphate relative to a control, said control comprising human CDC25 and p-nitrophenyl phosphate in the absence of said compound to be assessed;

wherein if human CDC25 present in the combination produced in acts upon p-nitrophenyl phosphate to an extend less by at least 5–10% than human CDC25 present in the control, the compound is an inhibitor of human CDC25 tyrosine phosphatase activity.

2. The method of claim 1, wherein the human CDC25 is a component of a fusion protein.

3. The method of claim 1, wherein the CDC25 from a human source is selected from the group consisting of: CDC25A, CDC25B, and CDC25C.

4. The method of claim 2, wherein the fusion protein is a glutathione-S-transferase/human CDC25 tyrosine phosphatase fusion protein.

* * * * *

UNITED STATES PATENT AND TRADEMARK OFFICE
CERTIFICATE OF CORRECTION

PATENT NO. : 5,294,538
DATED : March 15, 1994
INVENTOR(S) : Beach

It is certified that error appears in the above-identified patent and that said Letters Patent is hereby corrected as shown below:

Column 1, line 8, delete "GM69620" and insert --R01 GM39620--.

Signed and Sealed this

Sixth Day of January, 1998

Attest:

BRUCE LEHMAN

Attesting Officer          Commissioner of Patents and Trademarks